US012702779B2

(12) United States Patent
Longo

(10) Patent No.: US 12,702,779 B2
(45) Date of Patent: Aug. 11, 2026

(54) MEDICAL APPARATUS AND METHOD OF ADMINISTRATION AND REMOVAL OF FLUIDS FROM A PATIENT

(71) Applicant: DIVAA Medical Devices, LLC, Houston, TX (US)

(72) Inventor: Marc Longo, Houston, TX (US)

( * ) Notice: Subject to any disclaimer, the term of this patent is extended or adjusted under 35 U.S.C. 154(b) by 927 days.

(21) Appl. No.: 17/583,437

(22) Filed: Jan. 25, 2022

(65) Prior Publication Data

US 2022/0233800 A1 Jul. 28, 2022

Related U.S. Application Data

(60) Provisional application No. 63/141,697, filed on Jan. 26, 2021.

(51) Int. Cl.
*A61M 16/04* (2006.01)
*A61M 16/06* (2006.01)

(52) U.S. Cl.
CPC .... *A61M 16/0486* (2014.02); *A61M 16/0475* (2014.02); *A61M 16/0477* (2014.02); *A61M 16/0495* (2014.02); *A61M 16/0666* (2013.01)

(58) Field of Classification Search
CPC .......... A61M 16/0666; A61M 16/0461; A61M 16/0495; A61M 16/0486; A61M 16/0475; A61M 16/0477; A61M 2210/0625; A61M 16/0672
See application file for complete search history.

(56) References Cited

U.S. PATENT DOCUMENTS

| | | | | |
|---|---|---|---|---|
| 1,498,810 A * | 6/1924 | Poe | A61M 16/0493 | 128/207.14 |
| 3,756,244 A * | 9/1973 | Kinnear | A61M 16/0488 | 128/207.14 |
| 2004/0112383 A1* | 6/2004 | Curti | B29C 33/485 | 264/304 |
| 2006/0278238 A1* | 12/2006 | Borody | A61M 16/08 | 128/859 |
| 2007/0267024 A1* | 11/2007 | Kremer | A61M 16/0495 | 128/207.14 |
| 2012/0283513 A1* | 11/2012 | Leeflang | A61M 16/208 | 600/114 |
| 2013/0014754 A1* | 1/2013 | Guerra | A61M 16/0672 | 128/202.16 |
| 2013/0037026 A1* | 2/2013 | Miller | A61M 16/0493 | 128/204.18 |
| 2014/0135641 A1* | 5/2014 | Wachtell | A61M 16/021 | 128/203.14 |
| 2014/0323896 A1* | 10/2014 | McCauley | A61M 16/0493 | 128/207.14 |
| 2020/0113427 A1* | 4/2020 | Molnar | A61M 16/0402 | |
| 2020/0179632 A1* | 6/2020 | Worley | A61M 16/0672 | |
| 2020/0282164 A1* | 9/2020 | Thomas | A61M 16/0431 | |
| 2024/0066246 A1* | 2/2024 | Slaughter | A61M 16/085 | |

* cited by examiner

*Primary Examiner* — Brandy S Lee
*Assistant Examiner* — Sara K Toich

(57) ABSTRACT

Embodiments presented provide for a medical apparatus that allows for administration of a fluid, such as oxygen, to a patient, and to allow a medical professional to quickly and precisely administer such oxygen and/or a gaseous sedative with little waste.

10 Claims, 7 Drawing Sheets

MEDICAL APPARATUS AND METHOD OF ADMINISTRATION AND REMOVAL OF FLUIDS FROM A PATIENT

CROSS-REFERENCE TO RELATED APPLICATIONS

The present application claims priority to U.S. Provisional Application 63/141,697, dated Jan. 26, 2021, the entirety of which is incorporated by reference.

FIELD OF THE DISCLOSURE

Aspects of the disclosure relate to medical devices. More specifically, aspects of the disclosure relate to a medical apparatus configured to administer a fluid, such as a gas or mixture of gasses, as well as remove expired gasses from a patient. Such administration may be, for example, during a surgical procedure.

BACKGROUND

As time has passed, new and effective medical procedures are desired in the marketplace. There is a desire to have medical procedures become relatively simple and fault-free endeavors. There is also a desire to make such procedures more economically feasible for patients. Medical procedures can be complicated or may be relatively simple. For complicated medical procedures, in some instances, it is necessary to administer a sedative to a patient to allow the medical professionals the ability to perform the required procedure. The sedative can be in a form of a liquid, in minor surgical procedures, or may be in the form of a gas, in more complicated and/or delicate procedures.

While the process of anesthetizing a patient is well known, surprisingly, certain functions/procedures are performed by medical professionals in less than optimum ways. One of the more common procedures that occurs is the ventilation of a patient who is undergoing the medical procedure. Often, there are competing interests within an operating room. First, the surgeon wishes for a patient to be secure and non-moving on the operating table. When the patient is immobile, the surgeon can quickly, safely and precisely perform the needed work and minimize pain and discomfort to the patient, which in turn speeds recovery. To anesthetize a patient, the attending medical professional wishes to only sedate a patient to a minimum amount or level, as further or deeper anesthesia can be more problematic for a patient. For example, too deep of a sedation may complicate or prolong a recovery time. In other instances, too deep of a sedation can cause physical changes in the patient, presenting a different set of circumstances for the surgeon than originally intended. Thus, there is a need a correct and precise amount of sedation for a patient. In addition to the amount of sedation, oxygen must be provided to the patient to keep the patient with a high and stable blood oxygen content. Moreover, carbon dioxide that is exhaled by a patient must be removed and measured so that the process of inhalation may be started again and to assess the patient's respiratory status. The carbon dioxide removed may indicate the amount of respiration and effectiveness of respiration of the patient.

In a typical operating room, gasses are fed to a patient through an airway that is placed into the patient's oral cavity. A conventional apparatus that is similar in shape to a blunt plastic "fish hook" is placed to position the tongue in a way that it does not obstruct the airway and stabilizes the tongue. As is known in the profession, upon sedation, the tongue may become a blockage to the airway, therefore it is desired to secure the tongue in a configuration that prevents the tongue from becoming a blockage. While such "fish hook" apparatus have certain advantages of securing the tongue, such advantages are minimized by other issues. Gas is fed to the patient oral/nasal area through a series of plastic tubes that may be connected to an oxygen tank and/or sedation gases. Conventional technologies require medical professionals to try to attach the technology to the "fish hook" apparatus with the plastic tubing such that the oral cavity apparatus prevents the tongue from moving during surgery and to allow gases to enter the patient through the separate and distinct plastic tubing. Currently, there are no "combination" type devices that allow for tongue stabilization and fluid and gas administration to a patient. Current "state of the art" procedures involve medical personnel cobbling together different apparatus and gas supply options to meet a patient's needs. Such mixing and matching can result in many unfortunate occurrences, such as pinched air tubing hoses and leaking fluids and displacement of the nasal cannula during the procedure.

More than 100 million surgeries requiring airway based sedation occur in the United States alone every year. Thus, medical professionals are constantly trying to "mix and match" different options. Such trial-and-error results in large amounts of lost operating room time and wasted medical professional time, inconsistency in the quality of the administration of the fluids and the interruption of the surgery.

Trial and error procedures, moreover, can have dangerous consequences to members of the medical community and the public at large. As each patient may receive a different configuration, in some instances, the effectiveness of providing oxygen and sedation can vary. As some patients have more challenging physical or anatomical structures, such structures are something that attending medical professionals seek to overcome by increasing the amount or flow of treatment gases to a patient. In patients with a small airway, for example, supplying sufficient oxygen to the patient may be challenging. One obvious resolution to this issue, for example, would be to simply increase the supply of oxygen to a patient. This increase of oxygen supply, however, can be dangerous. Large amounts of oxygen may be pumped or stored in an operating room. Oxygen, a combustion source, can be ignited, for example, by the medical apparatus used by the surgeons themselves. In cases of facial surgery, for example, different types of electrical apparatus such as cauterizing equipment/lasers may be used. This equipment may have a large electrical draw and may generate sufficient heat to cause an ignition of the oxygen. During facial surgery, the oxygen and heat source are in very close proximity, significantly increasing the possibility of a fire. Fires in operating rooms are not uncommon and are a constant problem for medical professionals. As a result of the frequency of such fires, insurance rates for physicians can be very high, resulting in very expensive medical care and potential compromised patient safety There is a need to provide a medical apparatus and method of using a medical apparatus that will correctly administer fluids, such as gases to a patient.

There is a further need to provide a medical apparatus and method to remove carbon dioxide generated by a patient, wherein the removal of the carbon dioxide may be analyzed by an attending medical professional.

There is a still further need to provide a medical apparatus that will minimize the leaking of oxygen in an operating room, removing fire risk for medical professionals and patients alike. There is also a need to reduce insurance costs associated with such fire risks for the medical community at large.

There is also a need to provide a medical device that accomplishes the above, but that is still cost effective for patient treatment.

There is a further need to provide a medical device that can interact with standard medical apparatus used, eliminating the need for specialty treatment devices.

There is also a need to provide a medical device that is easily understandable by existing medical professionals and that requires minimal or no training for use.

There is a still further need to provide an apparatus and method that is easier to operate than conventional apparatus and methods and that eliminates trial-and-error procedures conducted by the medical community.

There is a further need to provide apparatus and methods that do not have the drawbacks discussed above.

SUMMARY

So that the manner in which the above recited features of the present disclosure can be understood in detail, a more particular description of the disclosure, briefly summarized below, may be had by reference to embodiments, some of which are illustrated in the drawings. It is to be noted that the drawings illustrate only typical embodiments of this disclosure and are therefore not to be considered limiting of its scope, for the disclosure may admit to other equally effective embodiments without specific recitation. Accordingly, the following summary provides just a few aspects of the description and should not be used to limit the described embodiments to a single concept.

In one example embodiment, an apparatus is disclosed comprising a body configured with a first end and a second end, a top surface and a bottom surface, the first end of the body configured to be inserted into an oral cavity of a patient. The body may comprise a first trunk line extending from the second end into the body. The body may further comprise a second trunk line extending from the second end into the body. The body may further comprise a first series of ports configured through at least a portion of the body connected to the first trunk line and a second series of ports configured through at least a second portion of the body connected to the second trunk line. The apparatus may also comprise a connection arrangement configured on the second end, wherein the connection arrangement is configured to attach an oral cannula to the body, the connection arrangement having at least two nose openings.

In another example embodiment, an apparatus is disclosed. The apparatus may comprise a body configured with a first end and a second end, a top surface and a bottom surface, the body having a curvature from 1 to 20 degrees as measured along a longitudinal axis and the first end of the body configured to be inserted into an oral cavity of a patient, the second end configured to protrude from the oral cavity of the patient. The body may further comprise a first series of ports configured through at least a portion of the body connected to the first trunk line and a second series of ports configured through at least a second portion of the body connected to the second trunk line. The body may also be configured with a first trunk line extending from the second end into the body connecting to the first series of ports. The body may also be configured with a second trunk line extending from the second end into the body connecting to the second series of ports, wherein the first trunk line and first series of ports and the second trunk line and second series of ports are configured to transport gases to and from the oral cavity of the patient. The apparatus may also be configured with a connection arrangement configured on the second end, wherein the connection arrangement is configured to attach an oral cannula to the body, the connection arrangement having at least two nose openings and a mouth opening and wherein the connection arrangement is leak tight such that gases entering and exiting the cannula do not leak from the connection arrangement.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the drawings. It is to be noted, however, that the appended drawings illustrate only typical embodiments of this disclosure and are therefore not be considered limiting of its scope, for the disclosure may admit to other equally effective embodiments.

Figure 1:
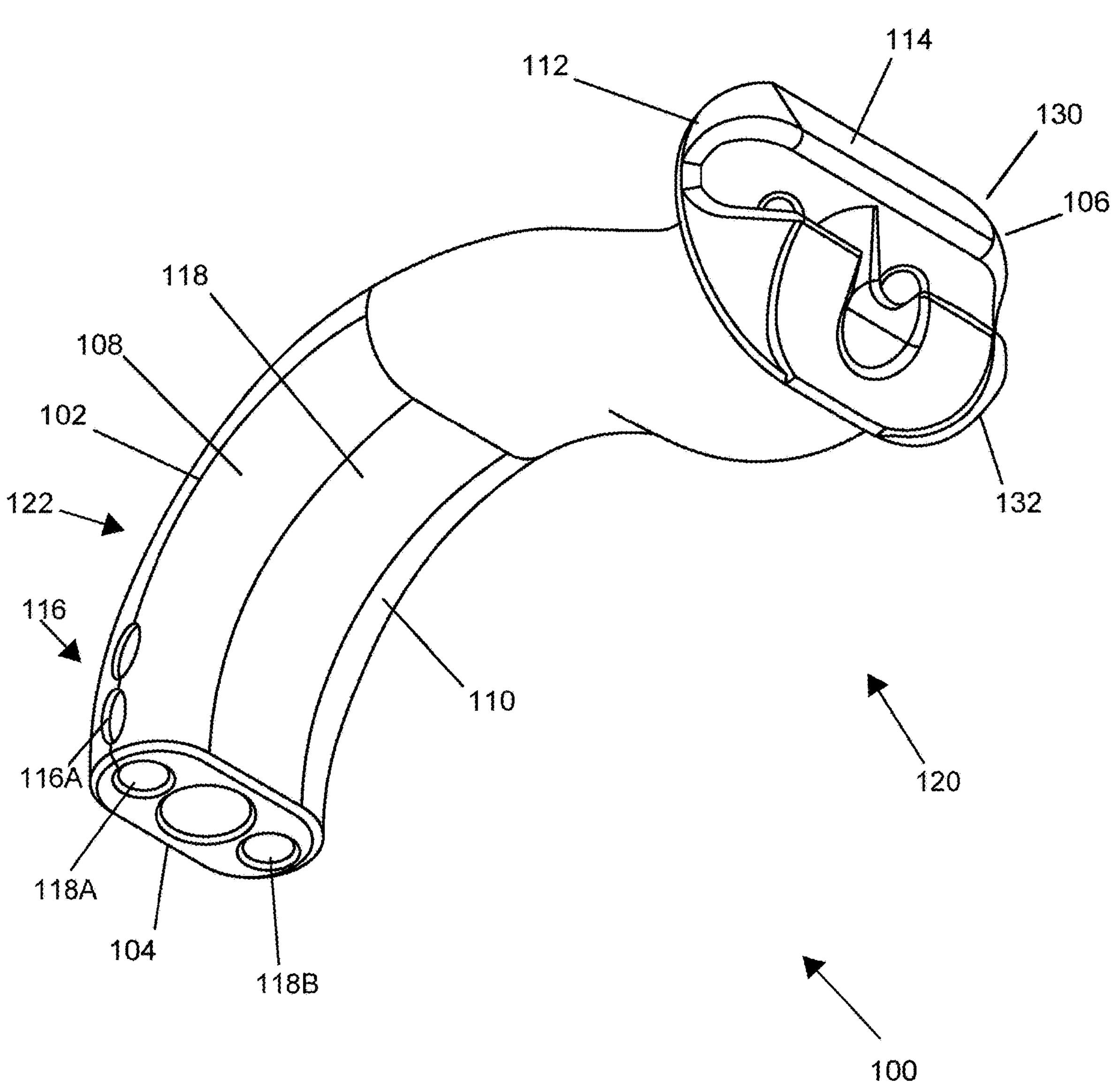
FIG. 1 is a perspective view of a medical apparatus in accordance with one example embodiment of the disclosure.

To facilitate understanding, identical reference numerals have been used, where possible, to designate identical elements that are common to the figures ("FIGS"). It is contemplated that elements disclosed in one embodiment may be beneficially utilized on other embodiments without specific recitation.

DETAILED DESCRIPTION

In the following, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the claims except where explicitly recited in a claim. Likewise, reference to "the disclosure" shall not be construed as a generalization of inventive subject matter disclosed herein and should not be considered to be an element or limitation of the claims except where explicitly recited in a claim.

Although the terms first, second, third, etc., may be used herein to describe various elements, components, regions, layers and/or sections, these elements, components, regions, layers and/or sections should not be limited by these terms. These terms may be only used to distinguish one element, components, region, layer or section from another region, layer or section. Terms such as "first", "second" and other numerical terms, when used herein, do not imply a sequence or order unless clearly indicated by the context. Thus, a first element, component, region, layer or section discussed herein could be termed a second element, component, region, layer or section without departing from the teachings of the example embodiments.

When an element or layer is referred to as being "on," "engaged to," "connected to," or "coupled to" another element or layer, it may be directly on, engaged, connected, coupled to the other element or layer, or interleaving elements or layers may be present. In contrast, when an element is referred to as being "directly on," "directly engaged to," "directly connected to," or "directly coupled to" another element or layer, there may be no interleaving elements or layers present. Other words used to describe the relationship between elements should be interpreted in a like fashion. As used herein, the term "and/or" includes any and all combinations of one or more of the associated listed terms.

Some embodiments will now be described with reference to the figures. Like elements in the various figures will be referenced with like numbers for consistency. In the following description, numerous details are set forth to provide an understanding of various embodiments and/or features. It will be understood, however, by those skilled in the art, that some embodiments may be practiced without many of these details, and that numerous variations or modifications from the described embodiments are possible. As used herein, the terms "above" and "below", "up" and "down", "upper" and "lower", "upwardly" and "downwardly", and other like terms indicating relative positions above or below a given point are used in this description to more clearly describe certain embodiments.

Referring to FIG. 1, an apparatus 100 is illustrated. The purpose of the apparatus 100 is to administer fluids, such as oxygen, to a patient during a medical procedure. Other fluids, such as sedation gases, may also be used. In addition to administering such fluids, the apparatus 100 may also be used to remove gases, such as carbon dioxide from a patient during the normal breathing process. As used herein, the fluid administered or removed may be combination of such gases. Differing gasses may be used, such as nitrous oxide, halothane, isoflurane, desflurane, sevoflurane. Nitrous oxide may be used as a relatively non-volatile gas. Halothane, isoflurane, desflurane, sevoflurane, however, are volatile gases that readily react with chemicals and heat, volatile anesthetics have low vapor pressures and high boiling points, meaning they are liquids at room temperature and so require vaporizers during administration. Such vaporization occurs and the resulting gas is mixed with oxygen and administered to the patient.

In embodiments, the apparatus 100 may be made of a plastic, such as a thermoplastic, that may be molded, stamped, blown or otherwise shaped to a desired configuration. Other non-limiting embodiments may be constructed of silicone. In other embodiments, the apparatus 100 may be made of nylon. The apparatus 100 may be created to be "reusable" such that the apparatus 100 may be decontaminated in an autoclave. The apparatus 100 may be sized to fit in an oral cavity of a patient, such as an adult. As will be understood, patients may be various sizes, such as a child or a fully grown adult, therefore the apparatus 100 may be configured in multiple types of sizes to fit patient needs. The apparatus 100, when made of plastic, may be discarded or appropriately recycled, minimizing waste from the operating room. On other instances, the apparatus 100 may be made of metallic materials that may be reused. In such configurations that are going to subjected to decontamination, the apparatus 100 may be placed in a sterilizing solution or be subjected to a heat above 120 degrees C. Such heat may be contemporaneous with administration of a water vapor, if necessary. In other embodiments, the administration of heat may also be accompanied with/by pressurization. In some embodiments, the pressurization may exceed thirty (30) pounds per square inch.

The apparatus 100 is configured with a body 102 that has a first end 104 and a second end 106. In this embodiment, the first end 104 is placed into an oral cavity of a patient that requires medical treatment, such as undergoing sedation. The apparatus 100 is configured to fit into the oral cavity and at least partially down the throat of the patent. A bottom side 110 of the apparatus 100 is configured to contact the tongue area of the patient and maintain this body structure in place during the sedation. As a result of this fixation, the tongue does not become a potential blockage to the patient's airway. The apparatus 100 is configured with a curvature 122 to allow for contact with the tongue throughout the oral cavity and pass down into the throat of the patient. In the embodiment, the amount of curvature shown is approximately 5 percent deviation from a longitudinal axis that runs parallel to the body 102 of the apparatus 100. Although shown as a 5 percent curvature, other configurations are possible. Greater or lesser amounts of curvature are possible. In some configurations, the amount of curvature may be zero. In still other configurations, the amount of curvature can vary along the length of the body 102. Thus, in one non-limiting embodiment, from the second end 106 to a mid-point of the apparatus 100, there may be no curvature at all, however from the mid-point of the apparatus 100 to the first end, a degree of curvature is provided. In other embodiments, several different degrees of curvature may be provided along the length of the body 102.

In embodiments, the body 102 may have different lengths, according to the needs of a patient. The body 102, in non-limiting embodiments, may have an overall length of 5.5 inches (13.97 centimeters). Different lengths, for example, may be achieved by reduction of 0.5 inches (1.27 centimeters) of length. Thus, the overall lengths, in non-limiting embodiments, may be 5.5 inches (13.97 centimeters), 5 inches (12.7 centimeters), 4.5 inches (11.43 centimeters), 4 inches (10.15 centimeters) and 3.5 inches (8.89 centimeters). The body 102 may be further configured with an overall width of 1.5 inches (3.81 centimeters), in one non-limiting embodiment. Overall widths may be decreased, for example, by 0.25 inches (0.635 centimeters). The above-identified sizes should not be considered limiting.

The body 102 is configured with a top surface 108 as well as a bottom surface 110. In one embodiment, the top surface 108 is generally not in contact with an interior surface of the patient, therefor the top surface 108 may be smooth in texture. The bottom surface 110 is intended to lie in contact with the patient and structures in the oral cavity, therefore the bottom surface 110 may be configured with a roughened surface to provide for increased friction, preventing the apparatus 100 from dislodging during use. The bottom surface 110 may also be configured to receive a temporary adhesive such that a seal is formed between the bottom surface 110 and the apparatus. Such optional seal may be a chemical seal, such as through use of a hydrogel mixture that may be removed upon completion of the surgical procedure.

Such hydrogel mixtures may include, but not be limited to, polyethylene glycol (PEG) polymers used in pulmonary surgery. As will be understood, use of a polyethylene glycol polymer would be used in instances where an extended period for the surgical operation would be carried out. In instances where surgical procedures would be considered an "out-patient" type of treatment, anchoring by chemical bonding may not be needed. As will be understood, aspects of the disclosure include treatment of different types of patients, including animals. Instances of using a chemical bond may also be used in patients, such as an animal, in a veterinary hospital, where different geometries are present in different breeds of dogs, cats, horses and other mammals as a non-limiting example. In the instance of large animals, a larger body 102 may be used for contact with the tongue area. Moreover, accompanying structures of the apparatus 100 may be increased according to the oxygen and sedation needs of the patient.

A connection arrangement 114 is located at the second end 106 of the apparatus 100. The purpose of the connection arrangement 114 is to provide a connection point for an oral cannula 700 (shown in FIG. 7) to the apparatus 100. The oral cannula 700 has the primary purpose of delivering gaseous mixtures to a patient that is undergoing surgery and/or recovery from medical maladies as well as providing an exhalation gas analysis by attached equipment. To this end, the oral cannula 700 is provided with a pair of nose lumens 702A and 702B and a single lumen oral trunk 704. The nose sections 702A, 702B and the oral trunk 704 are connected to a pair of tubes 706 that deliver fluids to and from the patient. The pair of tubes 706 are maintained in place with a slide bolo 708. One portion of the pair of tubes 706 may be configured with a filter 710 while the other portion of the tubes may be configured with a lock 712. The filter 710 may be configured to act as an anti-microbial filter to maintain a patient from sending and/or receiving pathogens into the surrounding air and operating room. The lock 712 may be used to connect to service gases, such as oxygen and sedation gases that are mixed at a mixing unit (not shown). The lock 712 provides a pressure tight seal to prevent escape of the gaseous mixture into the surrounding atmosphere. In one non-limiting embodiment, the lock 712 may be configured with a screw connection with a rubber or latex grommet to allow for a pressure tight connection to the oxygen and sedation gas supply. As illustrated, the connection arrangement 114 is configured to interface with a "dual cannula" configuration provided in FIG. 7, wherein a dual cannula configuration provides lumens for both nasal passages and mouth airway. In other embodiments, such as a "single cannula" configuration, the oral trunk 704 is omitted. In the instance where a single cannula is used, the connection arrangement 114 may be configured with openings that interface with only the nose sections 702A, 702B. In this configuration, ports for the oral trunk 704 may be omitted totally, or may be "blanked" off such that fluid flow is prevented through the connection arrangement 114 apportioned to the oral trunk 704. Such "blanking" may be accomplished by a tethered plug that may be inserted into the corresponding portion of the connection arrangement 114. The plug may be tethered to allow for foreign material exclusion from a patient such that the plug does not get lost inside a patient or become a choking hazard.

As will be understood, one of the nose lumens 702A is configured to supply oxygen and sedation gases. The other nose lumen 702B is configured to sample carbon dioxide. As will be further understood, the portions of the ports 116 on both sides of the apparatus 100 may be configured to supply oxygen to the nose lumen 702A and sample carbon dioxide through the other nose lumens 702B. In other configurations, the nose lumens 702A, 702B may be configured to both supply and/or remove gases.

As described above, in one embodiment, the oral cannula 700 is further configured to allow for transmission of exhaust gases from the patient. Such exhalation gases, such as carbon dioxide, can be measured by an attending medical physician using a capnography device. Such sampling may be monitored as may be done in moderate or heavy sedation surgery. Such monitoring through capnography, ensures that the patient maintains sufficient oxygen levels through the procedure. As will be understood, the filter 710 may be also used to prevent liquids from gathering within the sampling mechanism of the capnography device. Such liquids may be, for example, mucus and/or saliva. The oral cannula 700 may be configured with an end-tidal carbon dioxide sampling tubing ($ETCO_2$) on one side as well as an oxygen supply side on the other.

Referring to FIG. 1, the connection arrangement 114 is located at the second end 106 after passing through a throat area 120 from the mid-point of the apparatus 100. The throat area 120 may have several different geometries according to the needs of a patient. The throat area 120 may be a simple extension of the curvature 122 of the body 102 in some non-limiting embodiments. In other embodiments, a more "air-tight" seal may be required. In these embodiments, the throat area 120 may be configured in an expanded cone shape to fill the oral cavity and provide a binding force on all sides of the apparatus 100 during installation. The throat area 120 is followed by an expanded portion 112 that is configured to protrude from a patient's mouth and allow connection of the cannula 700, described in relation to FIG. 7.

In one example embodiment, the expanded portion 112 is configured with a elongated lip 130 that extends outwardly from a centerline of the second end 106. The extent of the protrusion of the elongated lip 130 may be varied due to the different geometries of patients. An exterior surface 132 of the elongated lip 130 may be created with a covering, in some non-limiting embodiments. The covering may be used to provide a soft interface between a patient's teeth/gum area and the exterior surface 132 of the apparatus 100. Such a configuration may be pliable, such as a rubber coating, to prevent marring a patient's teeth during the operation. As will be understood, other materials other than latex materials may be used, in cases where a patient may have sensitivity/allergies to latex compounds. In embodiments, the covering may be removable, at the discretion of the attending physician. As will be understood, the covering may also be interchangeable to provide a different profile, if necessary.

The apparatus 100 is configured with ports 116 (consisting of a first series of ports 116A and a second series of ports 116B) that are located along a periphery of the apparatus 100. The ports 116 are connected to respective trunk lines 118 (consisting of trunk lines 118A and 118B) that extends along a longitudinal axis of the apparatus 100. The trunk lines 118A and 118B are connected to the connection arrangement 114 such that gases entering the connection arrangement 114, for example through an oral cannula described in FIG. 7, pass through the trunk lines 118A and 118B and out the ports 116A and 116B. The number of ports 116 may be varied according to the needs of the patient. In the illustrated embodiment, five viewable ports 116 of seven total ports are provided near the first end 104 on the body 102. The diameter of the ports 116 may be varied such that a greater diameter port 116 may be utilized to transfer gases in larger volumes, such as those needed for a larger patient. A series of ports 116A may be configured to deliver oxygen and sedation gases via one trunk line 118A to the patient, while a second series of ports 116B may be configured to draw exhalation gases from the patient.

In other embodiments, the number of ports 116 and/or the diameter of the ports 116 may be reduced, thereby increasing the velocity of gases passing through the apparatus 100. Such embodiments may be needed, for example, when a patient has difficulty in providing their own respiration rate thereby necessitating a forced flow of gases into the patient. As will be understood, the ports 116 may be separated such that some ports are configured to withdraw carbon dioxide from a patient, while other ports 116 are configured to supply only gases being administered to the patient, wherein the different functions of the ports 116 may be mixed with ports 116 of other functions. Thus, in some embodiments, trunk lines 118 may be provided, one supplying gases to the patient, and the other removing gases from a patient so that the exhaust gases may be sampled through an ETCO2 connection to the oral cannula 700. As will be understood, in embodiments where a portion of the ports 116 provide oxygen and or sedation gas to a patient, while other portions of the ports 116 remove carbon dioxide from the patient, the ports 116 may be varied in diameter according to the gaseous flow rates required for the patient.

Figure 2:
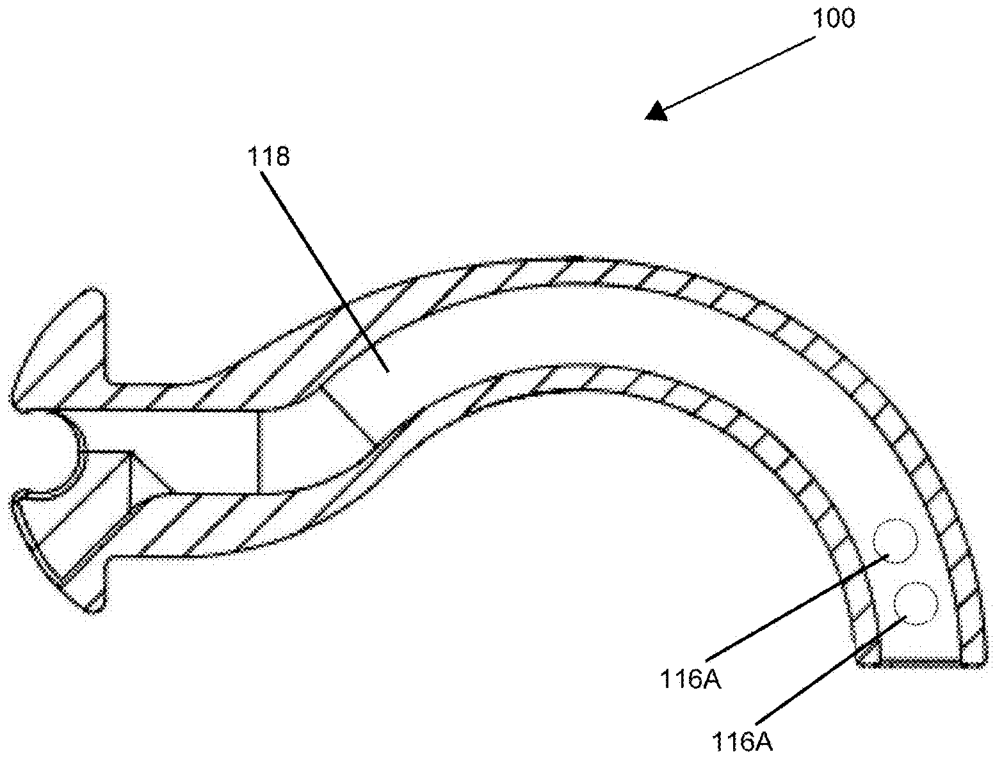
FIG. 2 is a cross-sectional view of the medical apparatus of FIG. 1.

Although not shown, in embodiments, the trunk lines 118 may be configured to progress beyond the area incorporating the ports 116 and extended to the first end 104. In such embodiments, an attending physician may apply a suction at the connection arrangement 114 that transfers down a trunk line 118 to the first end 104. Such suction may be useful in removing fluids that have gathered or are gathering in a patient's throat area during a surgical procedure. As will be understood, if trunk line 118 is provided, an internal valving may be used such that fluid flow is permitted in only one direction for the trunk line 118. For example, a check valve design may be implemented exhaust gases from attempting to travel up the ingress gases being supplied by the attending physician Referring to FIG. 2, a cross-section of the apparatus 100 is illustrated. The cross-section provides for trunk lines 118. The trunk lines 118 are illustrated as having a round cross-section. Other embodiments may be provided, such as an oval cross-section, a square cross-section, or a diamond shape as non-limiting embodiments. The ports 116 are connected to the trunk lines 118. The ports 116 are configured with a round cross-section. In other embodiments, the ports 116 may have different configurations. Such configurations may include oval, square, diamond or other complex shapes.

Figure 3:
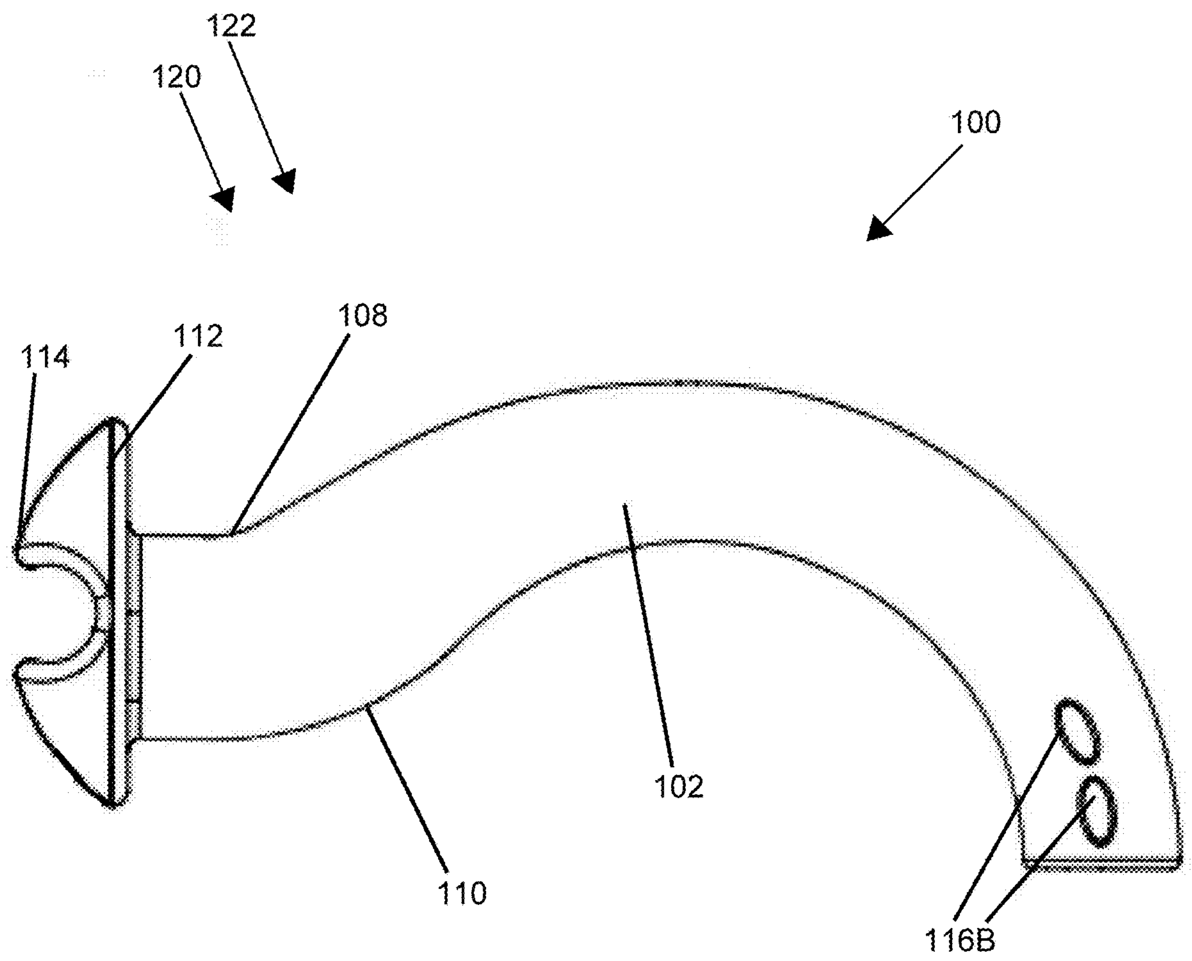
FIG. 3 is a side view of the medical apparatus of FIG. 1.

Referring to FIG. 3, a side elevational view of the apparatus 100 is illustrated. As described above, the amount of curvature 122 may be varied. In the illustrated embodiment, the amount of curvature 122 is 5 percent. As provided, the body 102 is a solid design made of a plastic material. Types of plastics may be, as non-limiting embodiments, thermoplastics, low density polyethylene, high density polyethylene, polypropylene, polyvinyl chloride, polyethylene terephthalate, polylactic acid-based plastics, polycarbonate, acrylic and acetal plastics as non-limiting embodiments. In embodiments, clear based plastics, such as an acrylic, may be chosen to allow for transparency to allow a medical professional to see the respiration of the patient. In embodiments, plastics may be biodegradable and/or recyclable.

In still further embodiments, the apparatus 100 plastics used may be color coded. For example, the body 102 of the apparatus 100 may have a color based upon the overall size of the apparatus 100. In a non-limiting embodiment, lighter colors may be used for smaller patients, while darker colors may be used for larger individuals. To this end, a medical professional may quickly and easily choose an appropriate size apparatus 100 for the application based upon the size of the individual and the color of the apparatus 100, thereby minimizing trial-and-error and potential waste of valuable medical resources.

Construction of the apparatus 100 may be through several construction methods. In one embodiment, the apparatus 100 may be configured through molding techniques. In other embodiments, the apparatus 100 may be through a blow molding technique. Other embodiments may allow for a three-dimensional printing of the apparatus 100. Still further embodiments provide for rotational molding, extrusion blow molding, reaction injection molding, vacuum casting, thermoforming, or compression molding, as non-limiting embodiments.

Figure 4:
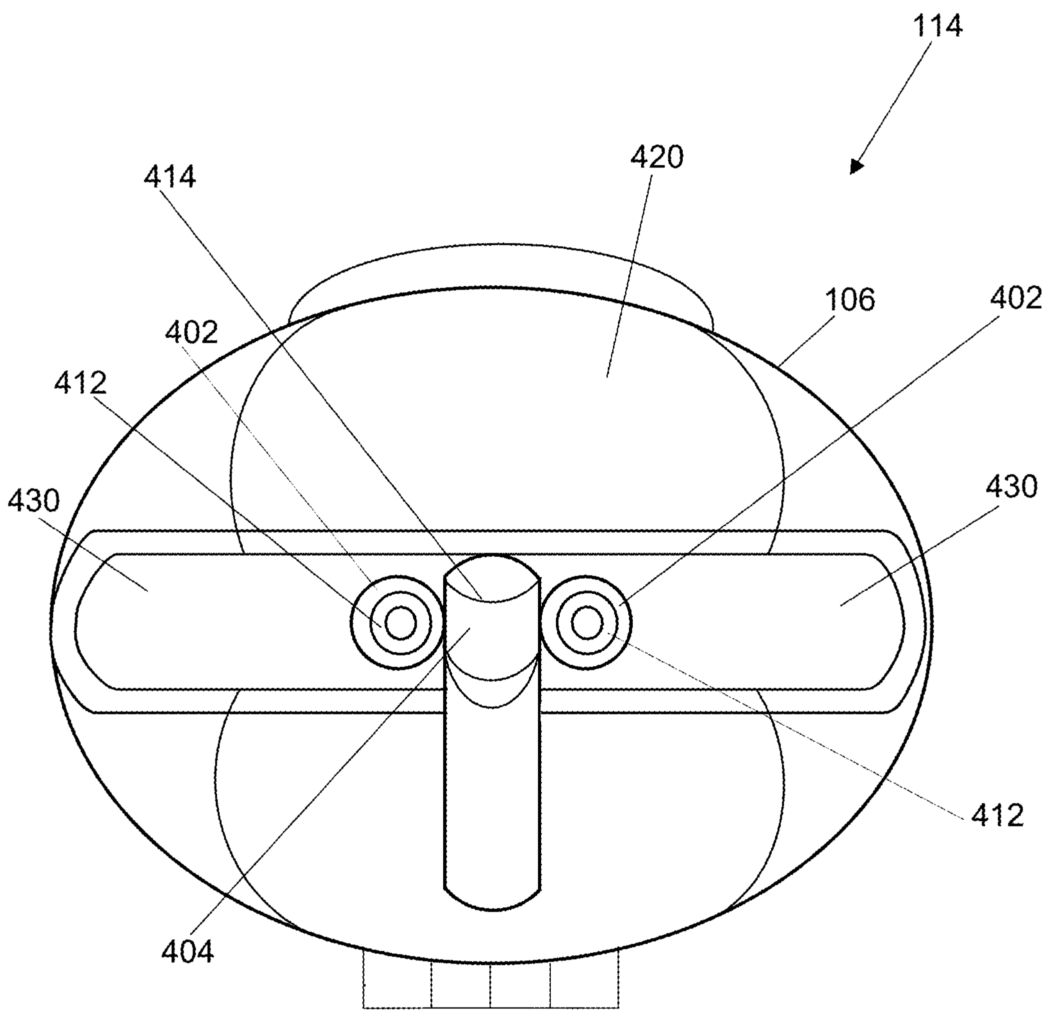
FIG. 4 is an expanded view of the connection arrangement of the medical apparatus of FIG. 1.
Figure 7A:
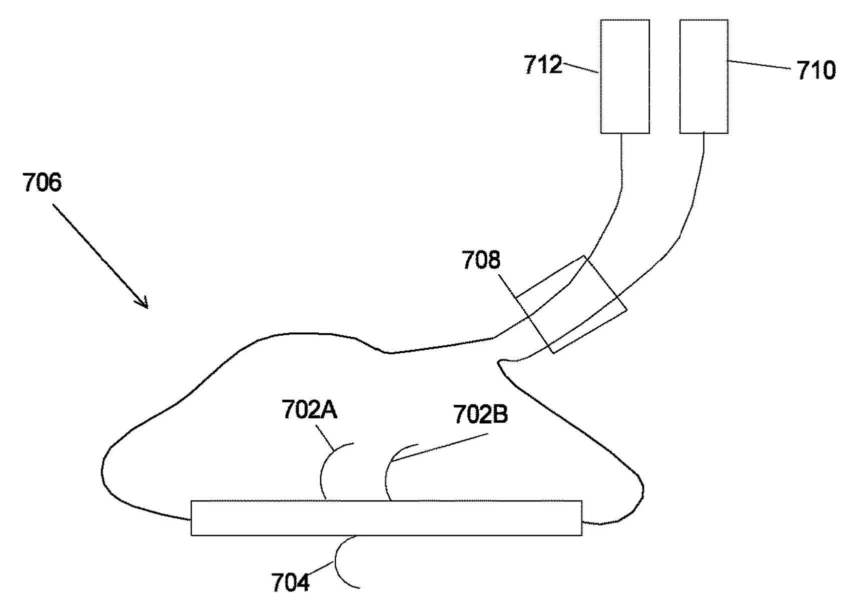
FIG. 7A is a perspective view of and oral cannula to be used to connect to the medical apparatus of FIG. 1.
Figure 7B:
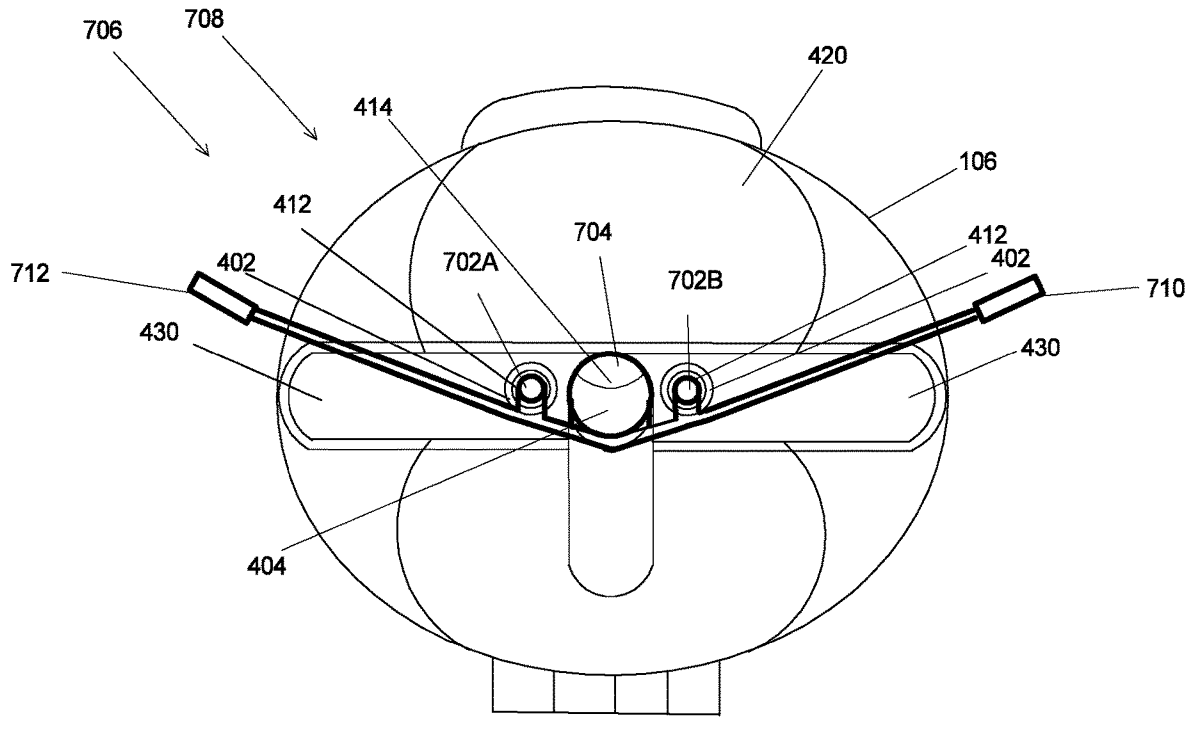
FIG. 7B is an exploded view of the connections to the medical apparatus of FIG. 1.

Referring to FIG. 4, the connection arrangement 114 is illustrated in more detail. The connection arrangement 114 is the portion of the apparatus 100 that connects to an oral cannula 700 as described in FIG. 7. A pair of nose openings 402 and a single mouth opening 404 are positioned in an indentation area 420 such that gases delivered by the oral cannula pass through the connection arrangement 114 and into the apparatus 100. As illustrated, the connection arrangement 114 is located at the second end 106 of the apparatus 100. Although shown as an indentation area 420, the area where the nose openings 402 and mouth opening 404 may be other configurations such as a flat configuration. A retainer 430 may be provided such that the oral cannula, as described in FIG. 7, is retained near the connection arrangement 114. This retainer 430 allows for quick connection of the oral cannula to the second end 106 of the apparatus 100. As will be understood, a nose orifice 412 may be installed in either one or both of the nose openings 402 at the second end 106. The purpose of the nose orifice 412 is to increase the velocity of gases traveling down the length of the apparatus 100. Thus, the nose orifice provides a restriction within the apparatus 100 to provide a jetting of gases down into the patient. In a similar design, a mouth orifice 414 may be installed within the mouth inlet 404 such that gas speed are increased along the body of the apparatus 100. In embodiments, the mouth orifice 414 and the nose orifice 412 may be removable such that different size orifices may be installed in their respective nose openings 402 and mouth opening 404. Although shown with a mouth opening 404, other embodiments of the second end 106 are possible, including deletion of the mouth opening 404. In such embodiments, the mouth opening 404 may be deleted altogether, or a plug may be installed within the mouth opening 404, rather than a mouth orifice 414. In embodiments using a plug, the plug, would prevent flow of gases entering the second and 106 at the mouth opening 404. In instances where a plug is used, the plug may be a friction fit design, or may be a tethered design such that the plug does not become a hazard to a patient.

In embodiments, the connection arrangement 114 is configured to prevent bending of the lumens 702A and 702B that connect to the connection arrangement 114. Prevention of the bending of the lumen 702A allows oxygen and sedation gases to flow uninterrupted. Additionally, prevention of bending of the lumen 702B allows for sampling of exhaust gases from the patient through capnography. In embodiments, the lumens 702A and 702B may be provided with ball ends that "snap" into the connection arrangement

114, wherein the connection arrangement 114 has a ball configured hollow portions that match the outside diameter of the ball ends of the lumens 702A and 702B, thereby providing a firm attachment of the lumens 702A, 702B to the apparatus 100. Moreover, a similar connection arrangement may be made for an oral lumen, is so equipped.

Figure 5:
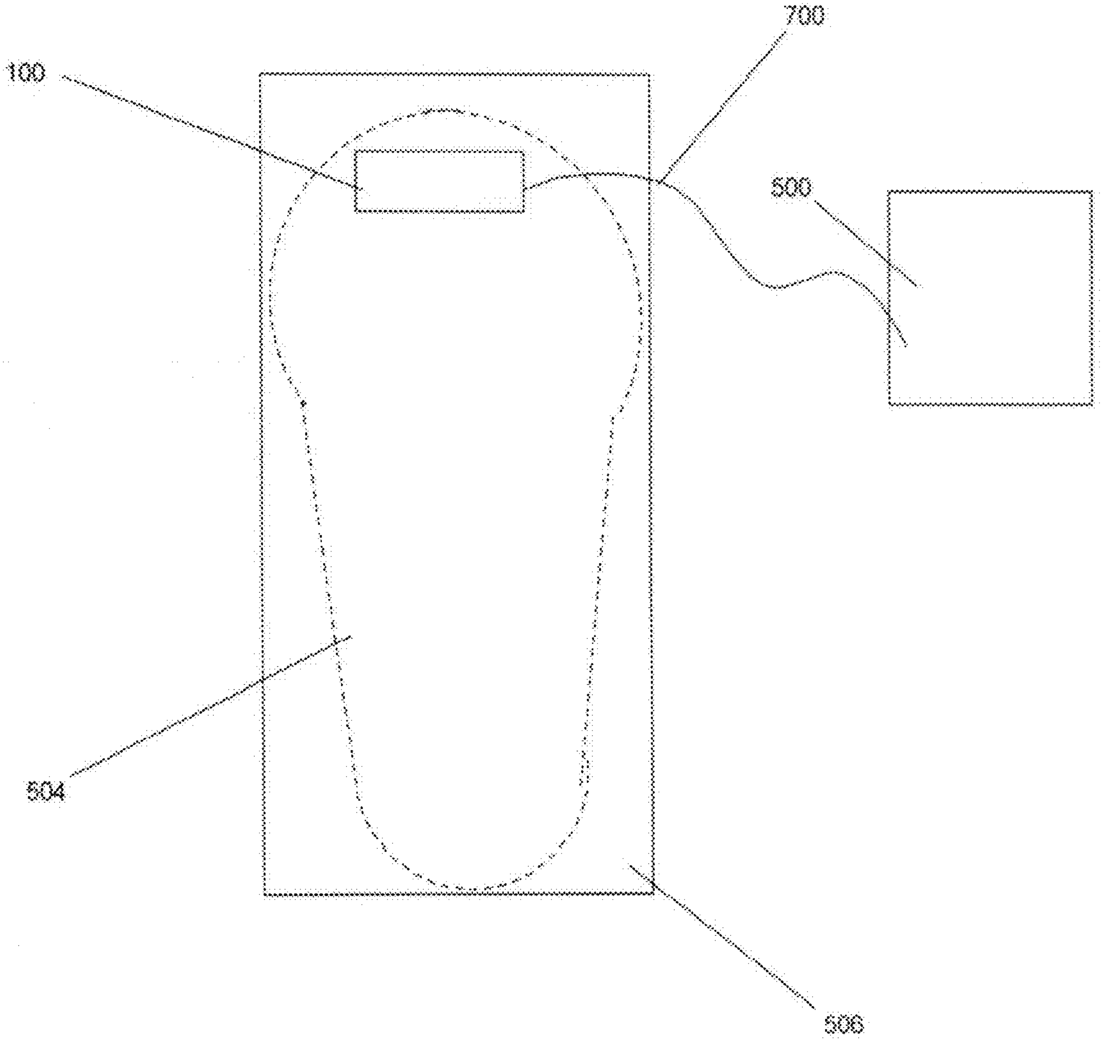
FIG. 5 is a diagrammatic layout of equipment used in an operating room setting, using the medical apparatus of FIG. 1.

Referring to FIG. 5, an overall layout of the environment that the apparatus 100 will be used in. In one non-limiting embodiment, a gaseous delivery system 500 is connected to a cannula 602 to transport oxygen and sedation gases from the delivery system 500 to a patient 504. Different sedation gases may be used, including nitrous oxide, halothane, sevoflurane, desflurane and isoflurane. The patient 504 may be supported by a table 506 that has elevational and incline control. In the example embodiment, the table 506 may be used in an "out-patient" configuration, wherein the patient will not need hospitalization after the surgery has been conducted. As described above, the apparatus 100 may be connected to the cannula 700, through various potential arrangements, including a retainer or through a "snap" fitting connecting the available portions of the cannula to the apparatus 100.

Figure 6:
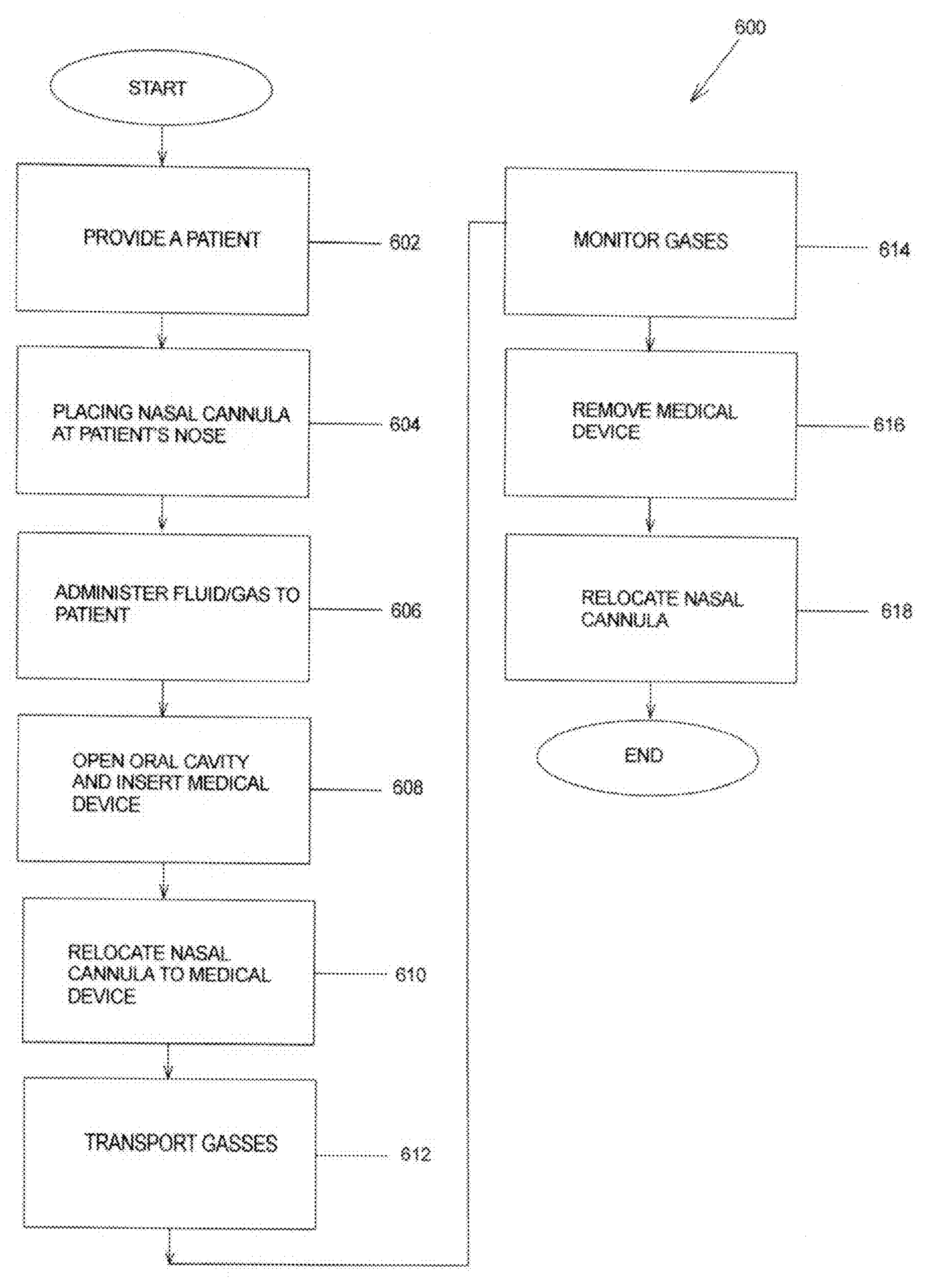
FIG. 6 is a method of administration and removal of fluids from a patient in accordance with an example embodiment of the disclosure.

Referring to FIG. 6, a method 600 for administration and removal of fluids from a patient is illustrated. As provided, the method 600 may use the apparatus 100, described in relation to FIG. 1. The method 600 provides for administration and removal of fluids from a patient. In this method, the fluids may be, for example, a mixture of oxygen and sedation gases. At 602, the method provides for providing a patient that requires administration of and removal of fluids. At 604, the method provides for opening an oral cavity of the patient. At 606, the method provides inserting a medical apparatus into the oral cavity of the patient such that the medical apparatus contacts at least a portion of the oral cavity of the patient and extends at least partly down a patient's throat and fixes a tongue of the patient when inserted. At 608, the method continues with connecting a cannula to the medical apparatus that has been inserted into the oral cavity of the patient. At 610, the method further continues with supplying a fluid to the cannula from a fluid source. At 612, the method further continues with transmitting the fluid through the cannula to the medical apparatus into a patient's respiratory system. At 614, the method may further continue with transporting respiratory gases from the patient out the medical apparatus to the cannula. At 616, the method may further continue wherein the transported respiratory gases are transmitted through the cannula to a monitoring station. At 618, the method may further continue with receiving the gases at the monitoring station. At 620, the method may further continue with monitoring the gases at the monitoring station.

Variations of the method 600, are possible. As will be understood, the cannula may be a singular nose-only cannula or a combination nose and mouth cannula arrangement. The cannula may be connected to the medical device prior to inserting the medical apparatus into the oral cavity of the patient. In a further embodiment, the connection of the cannula to the medical apparatus can be through a retainer configured to affix the cannula to the medical apparatus. The method may also provide for an embodiment for connecting a suction device to the medical apparatus, at the discretion of the attending medical professional. The suction device can be attached at any time, to provide for suction of the patient fluids. In embodiments, the suction device may be a positive displacement pump configured to allow for a constant/consistent vacuum draw. The patient fluids can be liquid or gases.

In further embodiments of the disclosure, a medical professional may apply an affixing material to a bottom surface of the medical apparatus prior to insertion of the medical apparatus into the oral cavity of the medical professional. In embodiments, the affixing material may be a hydrogel, in one non-limiting embodiment.

The aspects described above satisfy the needs of the industry and medical community at large. The aspects provide a medical device and method of using a medical device that will correctly administer fluids, such as gases to a patient.

Aspects of the disclosure also provide a medical device and method to remove carbon dioxide generated by a patient.

Aspects of the disclosure also provide a medical device that will minimize the leaking of oxygen in an operating room, removing fire risk for medical professionals and patients alike. Testing has been conducted upon one example embodiment, wherein the amount of oxygen and sedation gases are significantly reduced compared to conventional apparatus.

Aspects of the disclosure also provide a medical device that accomplishes the above, but that is still cost effective for patient treatment.

Aspects of the disclosure also provide a medical device that can interact with standard medical apparatus used, eliminating the need for specialty treatment devices.

Aspects of the disclosure also provide a medical device that is easily understandable by existing medical professionals and that requires minimal or no training for use.

Aspects of the disclosure also provide an apparatus and methods that is easier to operate than conventional apparatus and methods and that eliminate trial and error procedures conducted by the medical community.

Aspects disclosed provide an apparatus comprising a body configured with a first end and a second end, a top surface and a bottom surface, the first end of the body configured to be inserted into an oral cavity of a patient. The body may comprise a first trunk line extending from the second end into the body. The body may further comprise a second trunk line extending from the second end into the body. The body may further comprise a first series of ports configured through at least a portion of the body connected to the first trunk line and a second series of ports configured through at least a second portion of the body connected to the second trunk line. The apparatus may also comprise a connection arrangement configured on the second end, wherein the connection arrangement is configured to attach an oral cannula to the body, the connection arrangement having at least two nose openings.

In one non-limiting embodiment, the apparatus may be configured wherein the oral cannula has two nasal lumens.

In one non-limiting embodiment, the apparatus may be configured wherein the oral cannula has two nasal lumens and an oral lumen.

In one non-limiting embodiment, the apparatus may be configured wherein the body is configured of a plastic.

In one non-limiting embodiment, the apparatus may be configured wherein the bottom surface is roughened for contact with at least a portion of an oral cavity of the patient.

In one non-limiting embodiment, the apparatus may be configured wherein the body further comprises an expanded portion located at the second end, wherein the expanded portion is configured to protrude from the oral cavity of the patient.

In one non-limiting embodiment, the apparatus may be configured wherein the body is further configured with a curvature along a longitudinal axis of the body.

In another example embodiment, the apparatus may be configured wherein the curvature is between 1 degree and 20 degrees of curvature from the longitudinal axis of the body.

In another example embodiment, the apparatus may be configured wherein the body further comprises a throat area located adjacent to the second end.

In another example embodiment, the apparatus may be configured wherein the throat area is configured as an expanded cone shape.

In another example embodiment, the apparatus may be configured wherein the first series of ports are configured in one of a round, oval, diamond and square shape.

In another example embodiment, the apparatus may be configured wherein the second series of ports are configured in one of a round, oval, diamond and square shape.

In another example embodiment, the apparatus may be configured wherein the first series of ports is located on a side of the body.

In another example embodiment, the apparatus may be configured wherein the second series of ports is located on a side of the body.

In another example embodiment, the apparatus may be configured wherein the first series of ports is intermixed with the second series of ports.

In another example embodiment, the apparatus may be configured to further comprise at least one nose orifice placed within at least one of the nose openings.

In another example embodiment, the apparatus may be configured wherein the connection arrangement is configured with a mouth opening.

In another example embodiment, the apparatus may further comprise at least one orifice placed within the mouth opening.

In another example embodiment, the apparatus may further comprise at least one orifice placed within at least one nose opening.

In another example embodiment, an apparatus is disclosed. The apparatus may comprise a body configured with a first end and a second end, a top surface and a bottom surface, the body having a curvature from 1 to 20 degrees as measured along a longitudinal axis and the first end of the body configured to be inserted into an oral cavity of a patient, the second end configured to protrude from the oral cavity of the patient. The body may further comprise a first series of ports configured through at least a portion of the body connected to the first trunk line and a second series of ports configured through at least a second portion of the body connected to the second trunk line. The body may also be configured with a first trunk line extending from the second end into the body connecting to the first series of ports. The body may also be configured with a second trunk line extending from the second end into the body connecting to the second series of ports, wherein the first trunk line and first series of ports and the second trunk line and second series of ports are configured to transport gases to and from the oral cavity of the patient. The apparatus may also be configured with a connection arrangement configured on the second end, wherein the connection arrangement is configured to attach an oral cannula to the body, the connection arrangement having at least two nose openings and a mouth opening and wherein the connection arrangement is leak tight such that gases entering and exiting the cannula do not leak from the connection arrangement.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may be varied in many ways. Such variations are not to be regarded as a departure from the disclosure, and all such modifications are intended to be included within the scope of the disclosure.

While embodiments have been described herein, those skilled in the art, having benefit of this disclosure, will appreciate that other embodiments are envisioned that do not depart from the inventive scope. Accordingly, the scope of the present claims or any subsequent claims shall not be unduly limited by the description of the embodiments described herein.

What is claimed is:

1. An apparatus, comprising:

a body configured with a first end opening and a second end, a top surface and a bottom surface, the first end opening of the body configured to be inserted into an oral cavity of a patient and down a throat of the patient, the body comprising:

a first trunk line extending from and enclosed between the first end opening to the second end into the body;

a second trunk line extending from and enclosed between the first end opening to the second end into the body;

a first series of ports configured through at least a portion of the body connected to the first trunk line, the first series of ports extending from the first trunk line through a side of the body;

a second series of ports configured through at least a second portion of the body connected to the second trunk line, the second series of ports extending from the second trunk line through a second side of the body;

a mouth opening extending from the first end opening to the second end; and a connection arrangement configured on the second end, wherein the connection arrangement is configured to attach an oronasal cannula having two nasal cannulae and an oral cannula to the body, the connection arrangement having at least two nose openings and the mouth opening and wherein a first of the nose openings extends to the first trunk line to create a passage from the first end to the second end of the body and a second of the nose openings extends to the second trunk line from the first end to the second end of the body and wherein when a nasal cannulae are connected to the first and second nose openings, a leak tight seal is formed between the first end of the body through the body, the connection arrangement and into the nasal cannula and further wherein upon connection of the oral cannula to the mouth opening of the connection arrangement, a leak tight seal is formed from the first end of the body through the body, the connection arrangement and into the oral cannula to form a closed system and wherein a suction operation through the mouth opening can occur during use of the first and second nose openings.

2. The apparatus according to claim 1, wherein the body is configured of a plastic.

3. The apparatus according to claim 1, wherein the body further comprises:

an expanded portion located at the second end, wherein the expanded portion is configured to protrude from the oral cavity of the patient.

4. The apparatus according to claim 1, wherein the body is further configured with a curvature along a longitudinal axis of the body.

5. The apparatus according to claim 1, wherein the body further comprises:

a throat area located adjacent to the second end.

6. The apparatus according to claim 1, wherein the throat area is configured as an expanded cone shape.

7. The apparatus according to claim 1, wherein the first series of ports are configured in one of a round, oval, diamond and square shape.

8. The apparatus according to claim 1, wherein the second series of ports are configured in one of a round, oval, diamond and square shape.

9. The apparatus according to claim 1, further comprising:

at least one orifice placed within at least one nose opening.

10. An apparatus, comprising:

a body configured with a first end opening and a second end, a top surface and a bottom surface, the body having a curvature along a longitudinal axis and the first end of the body configured to be inserted into an oral cavity of a patient, the second end configured to protrude from the oral cavity of the patient, the body further comprising:

a first trunk line extending from and enclosed between the first end opening to the second end into the body connecting to a first series of ports;

a mouth opening extending from the first end to the second end;

a second trunk line extending from and enclosed between the first end opening to the second end into the body connecting to a second series of ports, wherein the first trunk line and the first series of ports and the second trunk line and the second series of ports are configured to transport gases to and from the oral cavity of the patient;

the first series of ports extending from the first trunk line through a side of the body;

the second series of ports extending from the second trunk line to a second side of the body; and a connection arrangement configured on the second end, wherein the connection arrangement is configured to attach an oronasal cannula having two nasal cannulae and an oral cannula to the body, the connection arrangement having at least two nose openings and a mouth opening and wherein the connection arrangement is leak tight such that gases entering and exiting the cannula do not leak from the connection arrangement and wherein a first of the nose openings extends to the first trunk line to create a passage from the first end to the second end of the body and a second of the nose openings extends to the second trunk line from the first end to the second end of the body and wherein when a nasal cannulae are connected to the first and the second nose openings, a leak tight seal is formed between the first end of the body through the body, the connection arrangement, and into the nasal cannula and further wherein upon connection of the oral cannula to the mouth opening of the connection arrangement, a leak tight seal is formed from the first end of the body through the body, the connection arrangement, and into the oral cannula to form a closed system and wherein a suction operation through the mouth opening can occur during use of the first and the second nose openings.

* * * * *